US008440196B1

(12) United States Patent
Funakoshi et al.

(10) Patent No.: US 8,440,196 B1
(45) Date of Patent: May 14, 2013

(54) TREATMENT FOR PANCREATITIS USING IL-6 RECEPTOR ANTAGONIST ANTIBODIES

(75) Inventors: Akihiro Funakoshi, Fukuoka (JP); Kyoko Miyasaka, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/762,550

(22) PCT Filed: Aug. 23, 1999

(86) PCT No.: PCT/JP99/04533
§ 371 (c)(1),
(2), (4) Date: Feb. 9, 2001

(87) PCT Pub. No.: WO00/10607
PCT Pub. Date: Mar. 2, 2000

(30) Foreign Application Priority Data

Aug. 24, 1998 (JP) .................................. 10-251796
Mar. 2, 1999 (JP) .................................. 11-054302

(51) Int. Cl.
*C07K 16/28* (2006.01)
*A61K 38/20* (2006.01)
*C12P 21/08* (2006.01)
*C07K 14/54* (2006.01)

(52) U.S. Cl.
USPC ..................... 424/145.1; 424/133.1; 530/351; 530/388.22

(58) Field of Classification Search .................. 530/350, 530/351, 387.9, 388.23; 424/85.2, 139.1, 424/143.1
See application file for complete search history.

(56) References Cited

U.S. PATENT DOCUMENTS 5,210,075 A  5/1993  Scholz et al.

FOREIGN PATENT DOCUMENTS

| EP | 0 572 118 | 12/1993 |
| EP | 0 617 126 A2 | 9/1994 |
| EP | 0 791 359 A1 | 8/1997 |
| JP | 03-219894 A | 9/1991 |
| WO | 92/19759 | 11/1992 |
| WO | WO 96/17869 A1 | 6/1996 |
| WO | WO 96/18648 A1 | 6/1996 |
| WO | WO 96/40966 A1 | 12/1996 |

OTHER PUBLICATIONS

K. Sato et al., "Reshaping a human antibody to inhibit the interleukin 6-dependent tumor cell growth", Cancer Research 53:851-856, Feb. 15, 1993.*
K. Reed et al., "Peptide YY suppresses serum IL-6 and TNF-alpha levels in murine necrotizing pancreatitis", Surgical Forum 48:179-180, 1997.*
G. Farkas et al., "Experimental acute pancreatitis results in increased blood-brain barrier permeability in the rat: a potential role for tumor necrosis factor and IL-6", Neuroscience Lett. 242:147-150, Feb. 20, 1998.*
A.N. Barclay et al., "The leukocyte antigen facts book", $2^{nd}$ edition. Academic Press, San Diego, 1997, pp. 498-499.*
M. Mihara et al., Clinical and Experimental Immunology 112(3) :397-402, published Jun. 1998, "IL-6 receptor blockage inhibits the onset of autoimmune kidney disease in NXB/WF1 mice".*
A.C. Knulst et al., Mediators of Inflammation 3:33-40, 1994.*
http://en.wikipedia.org/wiki/Interleukin_6 , accesssed May 9, 2009.*
Aderka et al., J. Imm. 143:3517-3523, 1989.*
Ulich et al., Am. J. Path 138:1097, 1991.*
Norman et al., Digestive Diseases and Sciences, 42:1783, 1997.*
A. Demols et al., JOP: J. Pancreas (Online), 4(1)49-57, 2003.*
Simms et al., "Polymorphonuclear Leukocyte Dysregulation During The Systemic Inflammatory Response Syndrome", Blood, 1994, pp. 1398-1407, vol. 83, No. 5, American Society of Hematology.
Gross et al., Inflammatory Mediators and Cytokines—New Aspects of the Pathophysiology and Assessment of Severity of Acute Pancreatitis?, Hepato-Gastroenterol, 1993, pp. 522-530, vol. 40, Georg Thieme Verlag Stuttgart, New York.
Suzuki et al., "Interleukin-6 (IL-6) Receptor Monoclonal Antibody Improved Severe Acute Pancreatitis in IL-6 Transgenic Mice", Gastroenterology, 1999, p. A1166 (Abstract), vol. 116, No. 4, Part 2, Gastroenterological Assoc.
Hendrix et al., "Selection of Hammerhead Ribozymes for Optimum Cleavage of Interleukin 6 mRNA", Biochemical Journal, 1996, pp. 655-661, vol. 314, No. 2, Printed in Great Britain.
Suzuki et al., "Induction of Acute Pancreatitis by Cerulein in Human IL-6 Gene Transgenic Mice", Pancreas, 2000, pp. 86-92, vol. 21, No. 1, Lippincoli Williams & Wilkins, Inc., Philadelphia.
Campbell et al.; "Islet Inflammation and Hyperplasia Induced by the Pancreatic Islet-specific Overexpression of Interleukin-6 in Transgenic Mice"; American Journal of Pathology; American Society for Investigative Pathology; vol. 145, No. 1; Jul. 1994; pp. 157-166.
Simms et al.; "Polymorphonuclear Leukocyte Dysregulation During the Systemic Inflammatory Response Syndrome"; Blood; The American Society of Hematology; vol. 83, No. 5; Mar. 1, 1994; pp. 1398-1407.
Alsfasser et al., "Decreased Inflammation and Improved Survival With Recombinant Human Activated Protein C Treatment in Experimental Acute Pacreatitis," (Reprinted) Arch. Surg., Jul. 2006, 141:670-676.
Bellomo, R., "The Cytokine Network in the Critically Ill," Anaesthesia and Intensive Care, Aug. 1992, 20(3):288-302.
Grewal et al., "Amelioration of the Physiologic and Biochemical Changes of Acute Pancreatitis Using an Anti-TNF-α Polyclonal Antibody," American Journal of Surgery, Jan. 1994, 167:214-219.
Gukovsky et al., "A rat model reproducing key pathological responses of alcoholic chronic pancreatitis," Am. J. Physiol. Gastrointest. Liver Physiol., 2008, 294:68-79, first published Sep. 20, 2007.

(Continued)

Primary Examiner — Lorraine Spector
(74) Attorney, Agent, or Firm — Foley & Lardner LLP (57) ABSTRACT

A preventive or therapeutic agent for pancreatitis said agent comprising as an active ingredient an interleukin-6 (IL-6) antagonist such as an antibody directed against IL-6 receptor.

12 Claims, 4 Drawing Sheets

OTHER PUBLICATIONS

Michalski et al,. "Cannabinoids Ameliorate Pain and Reduce Disease Pathology in Cerulein-Induced Acute Pancreatitis," Gastroenterology, May 2007, 132(5):1968-1978.

Mukaida et al., "Cytokines and The Immune Network," Clinical Test, May 1991, 35(5):447-452, with English translation, 14 pages.

Yamaguchi et al., "Risperidone Attenuates Local and Systemic Inflammatory Responses to Ameliorate Diet-Induced Severe Necrotic Pancreatitis in Mice: It May Provide a New Therapy for Acute Pancreatitis," J. Pharmacology and Experimental Therapeutics, 2009, 328(1):256-262.

Takaku et al,. *The Merck Manual 16$^{th}$ Ed.*, May 1, 1995, third printing, 760-766, with English abstract.

Tito et al. "Peptide YY ameliorates cerulean-induced pancreatic injury in the rat," Am. J. Surg., Jun. 1993, 65(6):690-696, 2 page Abstract.

Gross et al., "Inflammatory Mediators and Cytokines—New Aspects of the Pathophysiology and Assessment of Severity of Acute Pancreatitis?," Hepato-Gastroenterol, Georg Thieme Verlag Stuttgart, vol. 40, 1993, pp. 522-530.

\* cited by examiner

TREATMENT FOR PANCREATITIS USING IL-6 RECEPTOR ANTAGONIST ANTIBODIES

TECHNICAL FIELD

The present invention relates to a preventive or therapeutic agent for pancreatitis comprising an interleukin-6 (IL-6) antagonist as an active ingredient.

BACKGROUND ART

IL-6 is a cytokine which is also called B cell stimulating factor 2 (BSF2) or interleukin β2. IL-6 was discovered as a differentiation factor involved in the activation of B-lymphatic cells (Hirano, T. et al., Nature (1986) 324, 73-76). Thereafter, it was found to be a multifunctional cytokine that influences various functions of cells (Akira, S. et al., Adv. in Immunology (1993) 54, 1-78). IL-6 has been reported to induce the maturation of T-lymphatic cells (Lotz, M. et al., J. Exp. Immunol. (1988) 167, 1253-1258).

IL-6 transmits its biological activity through two types of proteins on the cell. One is IL-6 receptor, a ligand-biding protein with a molecular weight of about 80 kD, to which IL-6 binds (Taga, T. et al., J. Exp. Med. (1987) 166, 967-981; Yamasaki, K. et al., Science (1987) 241, 825-828). IL-6 receptor occurs not only in the membrane-bound form that penetrates through and is expressed on the cell membrane but also as a soluble IL-6 receptor consisting mainly of the extracellular region.

The other is a membrane-bound protein gp130 having a molecular weight of about 130 kD that is involved in non-ligand-binding signal transduction. IL-6 and IL-6 receptor form the IL-6/IL-6 receptor complex, which, after binding to gp130, transmits its biological activity to the cell (Taga, T. et al., Cell (1989) 58, 573-581).

An IL-6 antagonist is a substance that inhibits the transduction of biological activity of IL-6. As the IL-6 antagonist, there have been known so far antibody directed against IL-6 (anti-IL-6 antibody), antibody directed against IL-6 receptor (anti-IL-6 receptor antibody), and antibody directed against gp130 (anti-gp130 antibody), altered IL-6, partial peptides of IL-6 or IL-6 receptor and the like.

Anti-IL-6 receptor antibody has been described in several reports (Novick D. et al., Hybridoma (1991) 10, 137-146, Huang, Y. W. et al., Hybridoma (1993) 12, 621-630, International Patent Publication WO 95-09873, French Patent Application FR 2694767, U.S. Pat. No. 521,628). Humanized PM-1 antibody has been known that was obtained by grafting the complementarity determining region (CDR) of one of them, a mouse antibody PM-1 (Hirata, Y. et al., J. Immunology (1989) 143, 2900-2906), to a human antibody (the International Patent Publication WO 92-19759).

Pancreatitis is an inflammatory disease in which the activation of pancreatic enzymes causes autolysis in pancreatic tissues. There have been reported that the amount of IL-6 produced in the peripheral blood mononuclear cells is significantly high in patients with pancreatitis as compared to healthy normal humans, and that IL-6 production from the peripheral blood mononuclear cells is high in cases of acute pancreatitis with systemic complications as compared to those with no complications (de Beaux A. C. et al., Brit. J. Surgery, 83, 1071-5, 1996). Furthermore, since blood levels of IL-6 are higher and respond earlier than other parameters in severe cases of acute pancreatitis, they have been considered to be a prognostic indicator for severity of pancreatitis (Inagaki, T. et al., Pancreas, 14, 1-8, 1997).

It has been suggested that IL-1 and TNF closely correlate with the disease states, and mice lacking receptors to both of the cytokines do not suffer serious disease conditions, and show markedly decreased mortality rate (Denham, W. et al., Gastroenterology, 113, 1741-6, 1997). Attempts have been made to treat pancreatitis using these inhibitors in animal models (Norman, J. et al., Surgery, 117, 648-6755, 1995, Hughes, C. B. et al., American J. Surgery, 171, 274-280, 1996, Norman, J. et al., surgery, 120, 515-621, 1996).

However, no attempts have been made to specifically suppress the biological activity of IL-6 using IL-6 antagonists such as anti-IL-6 receptor antibody in pancreatitis, and it was unknown that IL-6 antagonists such as anti-IL-6 receptor antibody exhibit therapeutic effects on pancreatitis.

DISCLOSURE OF THE INVENTION

It is an object of the present invention to provide a preventive or therapeutic agent for pancreatitis said agent being free of the above-mentioned drawbacks.

Thus, the present invention provides (1) a preventive or therapeutic agent for pancreatitis comprising an IL-6 antagonist as an active ingredient.

The present invention also provides (2) a preventive or therapeutic agent for pancreatitis comprising an antibody directed against IL-6 receptor as an active ingredient.

The present invention also provides (3) a preventive or therapeutic agent for pancreatitis comprising a monoclonal antibody directed against IL-6 receptor as an active ingredient.

The present invention also provides (4) a preventive or therapeutic agent for pancreatitis comprising a monoclonal antibody directed against human IL-6 receptor as an active ingredient. The monoclonal antibody directed against human IL-6 receptor is preferably PM-1 antibody.

The present invention also provides (5) a preventive or therapeutic agent for pancreatitis comprising a monoclonal antibody directed against mouse IL-6 receptor as an active ingredient. The monoclonal antibody directed against mouse IL-6 receptor is preferably MR16-1 antibody.

The present invention also provides (6) a preventive or therapeutic agent for pancreatitis comprising a recombinant antibody directed against IL-6 receptor as an active ingredient. The recombinant antibody directed against IL-6 receptor has preferably a human antibody constant region (C region).

The present invention also provides (7) a preventive or therapeutic agent for pancreatitis comprising a chimeric or humanized antibody directed against IL-6 receptor as an active ingredient.

The present invention also provides (8) a preventive or therapeutic agent for pancreatitis comprising humanized PM-1 antibody as an active ingredient.

The present invention also provides (9) a preventive or therapeutic agent for acute or chronic pancreatitis comprising the IL-6 antagonist described in the above (1) to (8) as an active ingredient. Acute or chronic pancreatitis is, for example, severe or mild pancreatitis.

The present invention also provides (10) an agent for suppressing pancreatic edema, said agent comprising the IL-6 antagonist described in the above (1) to (8) as an active ingredient.

The present invention also provides (11) an agent for suppressing pancreatic edema, said agent comprising an antibody directed against IL-6 receptor described in the above (3) to (8) as an active ingredient.

BRIEF DESCRIPTION OF THE DRAWINGS

In FIG. 4, in contrast, the aggravation has been suppressed by the administration of an anti-IL-6 receptor antibody MR16-1.

BEST MODE FOR CARRYING OUT THE INVENTION

IL-6 antagonists for use in the present invention may be of any origin, any kind, and any form, as long as they have a preventive or therapeutic effect for pancreatitis, or an effect of controlling pancreatic edema.

IL-6 antagonists block signal transduction by IL-6 and inhibit the biological activity of IL-6. Preferably, IL-6 antagonists have an activity of inhibiting the binding of any of IL-6, IL-6 receptor, and gp130. As the IL-6 antagonists, there can be mentioned preferably anti-IL-6 antibody, anti-IL-6 receptor antibody, anti-gp130 antibody, altered IL-6, altered soluble IL-6 receptor, a partial peptide of IL-6 or IL-6 receptor, and low molecular weight substances having the same activity as these.

Anti-IL-6 antibodies for use in the present invention can be obtained as polyclonal or monoclonal antibodies using a known method. As the anti-IL-6 antibodies for use in the present invention, monoclonal antibodies of, in particular, a mammalian origin, are preferred. Monoclonal antibodies of a mammalian origin include those produced by a hybridoma and those produced by a host which has been transformed with an expression vector containing genetically engineered antibody genes. These antibodies, via binding to IL-6, block the binding of IL-6 to IL-6 receptor and, thereby, block signal transduction of the biological activity of IL-6 into the cell.

Examples of such antibodies include MH166 (Matsuda et al., Eur. J. Immunol. (1988) 18, 951-956) and SK2 antibody (Sato, K. et al., The 21st Nihon Mennekigakkai Soukai (General Meeting of the Japan Immunology Society), Academic Record (1991) 21, 166) and the like.

An anti-IL-6 antibody-producing hybridoma can be basically constructed using a known procedure as described below. Thus, IL-6 may be used as a sensitizing antigen and is immunized in the conventional method of immunization. The immune cells thus obtained are fused with known parent cells in the conventional cell fusion process, and then monoclonal antibody-producing cells are screened by the conventional screening method to prepare the desired hybridoma.

Specifically, anti-IL-6 antibody may be obtained in the following manner. For example, a human IL-6 for use as the sensitizing antigen to obtain antibody can be obtained using the IL-6 gene/amino acid sequence disclosed in Eur. J. Biochem (1987) 168, 543-550, J. Immunol. (1988) 140, 1534-1541, or Agr. Biol. Chem. (1990) 54, 2685-2688.

After a suitable host cell is transformed by inserting the IL-6 gene sequence into a known expression vector system, the IL-6 protein of interest is purified from the host cell or the culture supernatant thereof by a known method, and the purified IL-6 protein can be used as the sensitizing antigen. Alternatively, a fusion protein of the IL-6 protein and another protein may be used as the sensitizing antigen.

Anti-IL-6 receptor antibodies for use in the present invention can be obtained as polyclonal or monoclonal antibodies using a known method. As the anti-IL-6 antibodies for use in the present invention, monoclonal antibodies of, in particular, a mammalian origin, are preferred. Monoclonal antibodies of a mammalian origin include those produced by a hybridoma and those produced by a host which has been transformed with an expression vector containing genetically engineered antibody genes.

The antibodies, via binding to IL-6 receptor, inhibit the binding of IL-6 to IL-6 receptor, and thereby block the transduction of the biological activity of IL-6 into the cell.

Examples of such antibodies include MR16-1 antibody (Tamura, T., et al., Proc. Natl. Acad. Sci. USA (1993) 90, 11924-11928), PM-1 antibody (Hirata, et al., J. Immunology (1989) 143, 2900-2906), or AUK12-20 antibody, AUK64-7 antibody or AUK146-15 antibody (International Patent Publication WO 92-19759), and the like. Among them, PM-1 antibody is most preferred.

Incidentally, the hybridoma cell line which produces PM-1 antibody has been internationally deposited under the provisions of the Budapest Treaty as PM-1 on Jul. 10, 1990 with the National Institute of Bioscience and Human Technology, Agency of Industrial Science and Technology, of 1-3, Higashi 1-chome, Tsukuba city, Ibaraki pref., Japan, as FERM BP-2998. The hybridoma cell line which produces MR16-1 antibody has been internationally deposited under the provisions of the Budapest Treaty as MR16-1 on Mar. 13, 1997 with the National Institute of Bioscience and Human Technology, Agency of Industrial Science and Technology, of 1-3, Higashi 1-chome, Tsukuba city, Ibaraki pref., Japan, as FERM BP-5875.

Hybridomas producing anti-IL-6 receptor monoclonal antibody can be basically prepared using a known procedure as described bellow. Thus, IL-6 receptor is used as a sensitizing antigen and is immunized according to the conventional method of immunization. The immune cells thus obtained are fused with known parent cells in the conventional cell fusion process, and then monoclonal antibody-producing cells may be screened by the conventional screening method to prepare the desired hybridoma.

Specifically, anti-IL-6 receptor antibody may be prepared in the following manner. For example, human IL-6 receptor used as the sensitizing antigen for obtaining antibody can be obtained using the IL-6 receptor gene sequence/amino acid sequence disclosed in European Patent Application EP 325474, and mouse IL-6 receptor can be obtained using that disclosed in Japanese Unexamined Patent Publication (Kokai) 3 (1991)-155795.

There are two types of IL-6 receptor proteins: IL-6 receptor expressed on the cell membrane, and IL-6 receptor detached from the cell membrane (soluble IL-6 receptor) (Yasukawa et al., J. Biochem. (1990) 108, 673-676). Soluble IL-6 receptor antibody is composed substantially of the extracellular region of the IL-6 receptor bound to the cell membrane, and thereby is different from the membrane-bound IL-6 receptor in that the latter lacks the transmembrane region or both of the transmembrane region and the intracellular region. As the IL-6 receptor protein, any IL-6 receptor can be used, as long as it can be used a sensitizing antigen for production of the IL-6 receptor antibody for use in the present invention.

After the gene sequence of IL-6 receptor is inserted into a known expression vector system to transform an appropriate host cell, the desired IL-6 receptor protein may be purified from the host cell or a culture supernatant thereof using a known method. The purified IL-6 receptor protein thus purified may be used as the sensitizing antigen. Alternatively, cells that are expressing IL-6 receptor or a fusion protein of the IL-6 receptor protein and another protein may be used as the sensitizing antigen.

E. coli that has a plasmid pIBIBSF2R containing cDNA encoding human IL-6 receptor has been internationally deposited under the provisions of the Budapest Treaty as HB101-pIBIBSF2R on Jan. 9, 1989 with the National Institute of Bioscience and Human Technology, Agency of Industrial Science and Technology, of 1-3, Higashi 1-chome, Tsukuba city, Ibaraki pref., Japan, as FERM BP-2232.

Anti-gp130 antibodies for use in the present invention can be obtained as polyclonal or monoclonal antibodies using a known method. As the anti-gp130 antibodies for use in the present invention, monoclonal antibodies of, in particular, a mammalian origin, are preferred. Monoclonal antibodies of a mammalian origin include those produced by a hybridoma and those produced by a host which has been transformed with an expression vector containing genetically engineered antibody genes. The antibodies, via binding to gp130, inhibit the binding of IL-6/IL-6 receptor complex to gp130, and thereby block the transduction of the biological activity of IL-6 into the cell.

Examples of such antibodies include AM64 antibody (Japanese Unexamined Patent Publication (Kokai) 3 (1991)-219894), 4B11 antibody and 2H4 antibody (U.S. Pat. No. 5,571,513), B-S12 antibody and B-P8 antibody (Japanese Unexamined Patent Publication (Kokai) 8 (1996)-291199).

A monoclonal antibody-producing hybridoma can be basically created using a known procedure as described below. Thus, gp130 may be used as a sensitizing antigen and is immunized in the conventional method of immunization. The immune cells thus obtained are fused with known parent cells in the conventional cell fusion process, and then the monoclonal antibody-producing hybridomas are screened by the conventional screening method to prepare the desired hybridoma.

Specifically, monoclonal antibody may be obtained in the following manner. For example, gp130 used as the sensitizing antigen for antibody generation can be obtained using the gp130 gene sequence/amino acid sequence disclosed in European Patent Application EP 411946.

After a suitable host cell is transformed by inserting the gp130 gene sequence into a known expression vector system, the gp130 protein of interest is purified from the host cell or from the culture supernatant thereof. The purified gp130 receptor protein can be used as the sensitizing antigen. Alternatively, a fusion protein of the gp130 protein and another protein may be used as the sensitizing antigen.

Though mammals to be immunized with the sensitizing antigen are not specifically limited, they are preferably selected in consideration of their compatibility with the parent cell for use in cell fusion. They generally include rodents such as mice, rats, hamsters and the like.

Immunization of animals with a sensitizing antigen is carried out using a known method. A general method, for example, involves the intraperitoneal or subcutaneous administration of a sensitizing antigen to the mammal.

Specifically, a sensitizing antigen which has been diluted and suspended in an appropriate amount of phosphate buffered saline (PBS) or physiological saline etc. is mixed, as desired, with an appropriate amount of a common adjuvant, for example Freund's complete adjuvant. After being emulsified, it is preferably administered to a mammal several times every 4 to 21 days. Alternatively a suitable carrier may be used at the time of immunization of the sensitizing antigen.

After immunization and the confirmation of the increase in the desired antibody levels in the serum, the immune cells are taken out from the mammal and are subjected to cell fusion. Preferred immune cells subjected to cell fusion include in particular the spleen cells.

The mammalian myeloma cells as the other parent cells which are subjected to cell fusion with the above-mentioned immune cells preferably include various known cell lines such as P3X63Ag8.653) (Kearney, J. F. et al., J. Immunol. (1979) 123: 1548-1550), P3X63Ag8U.1 (Current Topics in Microbiology and Immunology (1978) 81: 1-7), NS-1 (Kohler, G. and Milstein, C., Eur. J. Immunol. (1976) 6: 511-519), MPC-11 (Margulies, D. H. et al., Cell (1976) 8: 405-415), SP2/0 (Shulman, M. et al., Nature (1978) 276: 269-270), FO (de St. Groth, S. F. et al., J. Immunol. Methods (1980) 35: 1-21), S194 (Trowbridge, I. S., J. Exp. Med. (1978) 148: 313-323), 8210 (Galfre, G. et al., Nature (1979) 277: 131-133) and the like.

Cell fusion between the above immune cells and the myeloma cells may be essentially conducted in accordance with a known method such as that described in Milstein et al. (Kohler, G. and Milstein, C., Methods Enzymol. (1981) 73: 3-46).

More specifically, the above cell fusion is carried out in the conventional nutrient broth in the presence of, for example, a cell fusion accelerator. As the cell fusion accelerator, for example, polyethylene glycol (PEG), Sendai virus (HVJ) and the like may be used, and, in addition, an adjuvant such as dimethyl sulfoxide etc. may be added as desired to enhance the efficiency of fusion.

The preferred ratio of the immune cells and the myeloma cells to be used is, for example, 1 to 10 times more immune cells than the myeloma cells. Examples of culture media to be used for the above cell fusion include RPMI1640 medium and MEM culture medium suitable for the growth of the above myeloma cell lines, and the conventional culture medium used for this type of cell culture, and besides a serum supplement such as fetal calf serum (FCS) may be added.

In cell fusion, predetermined amounts of the above immune cells and the myeloma cells are mixed well in the above culture liquid, to which a PEG solution previously heated to about 37° C., for example a PEG solution with a mean molecular weight of about 1000 to 6000, is added at a concentration of 30 to 60% (w/v) and mixed to obtain the desired fusion cells (hybridomas). Then, by repeating the sequential addition of a suitable culture liquid and centrifugation to remove the supernatant, cell fusion agents etc. which are undesirable for the growth of the hybridoma can be removed.

Said hybridoma is selected by culturing in the conventional selection medium, for example, the HAT culture medium (a culture liquid containing hypoxanthine, aminopterin, and thymidine). Culturing in said HAT culture medium is continued generally for a period of time sufficient to effect killing of the cells other than the desired hybridoma (non-fusion cells), generally several days to several weeks. The conventional limiting dilution method is conducted in which the hybridomas that produce the desired antibody are screened and monclonally cloned.

In addition to obtaining the above hybridoma by immunizing an animal other than the human with an antigen, it is also possible to sensitize human lymphocytes in vitro with desired antigen or desired antigen-expressing cells, and the resulting sensitized B lymphocytes are fused with a human myeloma cell for example U266, to obtain the desired human antibody having the activity of binding to desired antigen or desired antigen-expressing cells (see Japanese Post-examined Patent Publication (Kokoku) No. 1 (1989)-59878). Furthermore, a transgenic animal having a repertoire of all human antibody genes is immunized with the antigen or the antigen-expressing cells to obtain the desired human antibody in the method described above (see International Patent Publication WO 93/12227, WO 92/03918, WO 94/02602, WO 94/25585, WO 96/34096 and WO 96/33735).

The monoclonal antibody-producing hybridomas thus constructed can be subcultured in the conventional culture liquid, or can be stored for a prolonged period of time in liquid nitrogen.

In order to obtain monoclonal antibodies from said hybridoma, a method can be used in which said hybridoma is cultured in the conventional method and the antibodies are obtained as the supernatant, or a method in which the hybridoma is administered to and grown in a mammal compatible with said hybridoma and the antibodies are obtained as the ascites. The former method is suitable for obtaining high-purity antibodies, whereas the latter is suitable for a large scale production of antibodies.

Specifically a hybridoma producing anti-IL-6 receptor antibody can be constructed using the method disclosed in Japanese Unexamined Patent Publication (Kokai) 3 (1989)-139293. It can be conducted by a method in which the PM-1 antibody-producing hybridoma that was internationally deposited under the provisions of the Budapest Treaty as FERM BP-2998 on Jul. 10, 1990 with the National Institute of Bioscience and Human Technology, Agency of Industrial Science and Technology, of 1-3, Higashi 1-chome, Tsukuba city, Ibaraki pref., Japan, is intraperitoneally injected to BALB/c mice (manufactured by CLEA Japan) to obtain the ascites from which the PM-1 antibody is purified, or a method in which said hybridoma is cultured in a suitable culture medium such as the RPMI1640 medium containing 10% bovine fetal serum and 5% MB-Condimed H1 (manufactured by Boehringer Mannheim), the hybridoma SFM medium (manufactured by GIBCO-BRL), the PFHM-II medium (manufactured by GIBCO-BRL) and the like, and the PM-1 antibody can be purified from the culture supernatant.

A recombinant antibody which was produced by the recombinant gene technology in which an antibody gene was cloned from the hybridoma and integrated into a suitable vector which was then introduced into a host can be used in the present invention as monoclonal antibody (see, for example, Borrebaeck C. A. K., and Larrick J. W. THERAPEUTIC MONOCLONAL ANTIBODIES, published in the United Kingdom by MACMILLAN PUBLISHERS LTD. 1990).

Specifically, mRNA encoding the variable region (V) of the desired antibody is isolated from antibody-producing cells such as a hybridoma. The isolation of mRNA is conducted by preparing total RNA using, for example, a known method such as the guanidine ultracentrifuge method (Chirgwin, J. M. et al., Biochemistry (1979) 18, 5294-5299), the AGPC method (Chomczynski, P. et al., Anal. Biochem. (1987) 162, 156-159), and then mRNA is purified from the total RNA using the mRNA Purification kit (manufactured by Pharmacia) and the like. Alternatively, mRNA can be directly prepared using the Quick Prep mRNA Purification Kit (manufactured by Pharmacia).

cDNA of the V region of antibody may be synthesized from the mRNA thus obtained using a reverse transcriptase. cDNA may be synthesized using the AMV Reverse Transcriptase First-strand cDNA Synthesis Kit and the like. Alternatively, for the synthesis and amplification of cDNA, the 5'-Ampli FINDER RACE Kit (manufactured by Clontech) and the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) that employs polymerase chain reaction (PCR) may be used. The desired DNA fragment is purified from the PCR product obtained and may be ligated to vector DNA. Moreover, a recombinant vector is constructed therefrom and then is introduced into E. coli etc., from which colonies are selected to prepare the desired recombinant vector. The base sequence of the desired DNA may be confirmed by a known method such as the dideoxy method.

Once the DNA encoding the V region of the desired antibody has been obtained, it may be ligated to DNA encoding the constant region (C region) of the desired antibody, which is then integrated into an expression vector. Alternatively, the DNA encoding the V region of the antibody may be integrated into an expression vector which already contains DNA encoding the C region of the antibody.

In order to produce the antibody for use in the present invention, the antibody gene is integrated as described below into an expression vector so as to be expressed under the control of an expression regulatory region, for example an enhancer and/or a promoter. Subsequently, the expression vector may be transformed into a host cell and the antibody can then be expressed therein.

In accordance with the present invention, artificially altered recombinant antibody such as chimeric antibody and humanized antibody can be used for the purpose of lowering heterologous antigenicity against humans. These altered antibodies can be produced using known methods.

Chimeric antibody can be obtained by ligating the thus obtained DNA encoding the V region of antibody to DNA encoding the C region of human antibody, which is then integrated into an expression vector and introduced into a host for production of the antibody therein (see European Patent Application EP 125023, and International Patent Publication WO 92-19759). Using this known method, chimeric antibody useful for the present invention can be obtained.

For example, the plasmid that contains DNA encoding the L chain V region or the H chain V region of chimeric PM-1 antibody was designated as pPM-k3 or pPM-hl, respectively, and E. coli having the plasmid has been internationally deposited under the provisions of the Budapest Treaty as NCIMB 40366 and NCIMB 40362, respectively, on Feb. 11, 1991 with the National Collections of Industrial and Marine Bacteria Limited.

Humanized antibody which is also called reshaped human antibody has been generated by transplanting the complementarity determining region (CDR) of antibody of a mammal other than the human, for example mouse antibody, into the CDR of human antibody. The general recombinant DNA technology for preparation of such antibodies is also known (see European Patent Application EP 125023 and International Patent Publication WO 92-19759).

Specifically, a DNA sequence which was designed to ligate the CDR of mouse antibody with the framework region (FR) of human antibody is synthesized from several divided oligonucleotides having sections overlapping with one another at the ends thereof. The DNA thus obtained is ligated to the DNA encoding the C region of human antibody and then is integrated into an expression vector, which is introduced into a host for antibody production (see European Patent Application EP 239400 and International Patent Publication WO 92-19759).

For the FR of human antibody ligated through CDR, the complementarity determining region that forms a favorable antigen binding site is selected. When desired, amino acids in the framework region of the antibody variable region may be substituted so that the complementarity determining region of reshaped human antibody may form an appropriate antigen biding site (Sato, K. et al., Cancer Res. (1993) 53, 851-856).

For example, for chimeric antibody or humanized antibody, the C region of human antibody is used. As the C region of human antibody, there can be mentioned Cγ, and, for example, Cγ1, Cγ2, Cγ3, and Cγ4 can be used. The C region of human antibody may be modified to improve the stability of antibody or the production thereof.

Chimeric antibody consists of the variable region of antibody derived from a mammal other than the human and the C region derived from human antibody, whereas humanized antibody consists of the complementarity determining region of antibody derived from a mammal other than the human and the framework region and the C region derived from human antibody. Accordingly, antigenicity thereof in the human body has been reduced so that they are useful as antibody for use in the present invention.

A preferred embodiment of the humanized antibody for use in the present invention includes humanized PM-1 antibody (see International Patent Publication WO 92-19759).

Antibody genes constructed as described above may be expressed and obtained in a known method. In the case of mammalian cells, expression may be accomplished using a vector containing a commonly used useful promoter, the antibody gene to be expressed, and DNA in which the poly A signal has been operably linked at 3' downstream thereof or a vector containing said DNA. Examples of the promoter/enhancer include human cytomegalovirus immediate early promoter/enhancer.

Additionally, as the promoter/enhancer which can be used for expression of antibody for use in the present invention, there are viral promoters/enhancers such as retrovirus, polyoma virus, adenovirus, and simian virus 40 (SV40), and promoters/enhancers derived from mammalian cells such as human elongation factor 1α (HEF1α).

For example, expression may be readily accomplished by the method of Mulligan et al. (Mulligan, R. C. et al., Nature (1979) 277, 108-114) when SV40 promoter/enhancer is used, or by the method of Mizushima et al. (Mizushima, S. and Nagata, S, Nucleic Acids Res. (1990) 18, 5322) when HEF1α promoter/enhancer is used.

In the case of *E. coli*, expression may be conducted by operably linking a commonly used useful promoter, a signal sequence for antibody secretion, and the antibody gene to be expressed, followed by expression thereof. As the promoter, for example, there can be mentioned lacz promoter and araB promoter. The method of Ward et al. (Ward, E. S. et al., Nature (1098) 341, 544-546; Ward, E. S. et al., FASEB J. (1992) 6, 2422-2427) may be used when lacz promoter is used, and the method of Better et al. (Better, M. et al., Science (1988) 240, 1041-1043) may be used when araB promoter is used.

As the signal sequence for antibody secretion, when produced in the periplasm of *E. coli*, the pelB signal sequence (Lei, S. P. et al., J. Bacteriol. (1987) 169, 4379-4383) can be used. After separating the antibody produced in the periplasm, the structure of the antibody is appropriately refolded before use (see, for example, WO 96/30394).

As the origin of replication, there can be used those derived from SV40, polyoma virus, adenovirus, bovine papilloma virus (BPV) and the like. Furthermore, for the amplification of the gene copy number in the host cell system, expression vectors can include as selectable markers the aminoglycoside phosphotransferase (APH) gene, the thymidine kinase (TK) gene, *E. coli* xanthine guaninephosphoribosyl transferase (Ecogpt) gene, the dihydrofolate reductase (dhfr) gene and the like.

For the production of antibody for use in the present invention, any production system can be used. The production system of antibody preparation comprises the in vitro or the in vivo production system. As the in vitro production system, there can be mentioned a production system which employs eukaryotic cells and the production system which employs prokaryotic cells.

When the eukaryotic cells are used, there are the production systems which employ animal cells, plant cells, and fungal cells. Known animal cells include (1) mammalian cells such as CHO cells, COS cells, myeloma cells, baby hamster kidney (BHK) cells, HeLa cells, and Vero cells, (2) amphibian cells such as *Xenopus* oocytes, or (3) insect cells such as sf9, sf21, and Tn5. Known plant cells include, for example, those derived from *Nicotiana tabacum*, which may be subjected to callus culture. Known fungal cells include yeasts such as the genus *Saccharomyces*, more specifically *Saccharomyces ceriviceae*, or filamentous fungi such as the genus *Aspergillus*, more specifically *Aspergillus niger*.

When the prokaryotic cells are used, there are the production systems which employ bacterial cells. Known bacterial cells include *Escherichia coli* (*E. coli*), and *Bacillus subtilis*.

By introducing via transformation the gene of the desired antibody into these cells and culturing the transformed cells in vitro, the antibody can be obtained. Culturing is conducted by a known method. For example, as the culture liquid, DMEM, MEM, RPMI1640, and IMDM can be used, and serum supplements such as fetal calf serum (FCS) may be used in combination. In addition, antibodies may be produced in vivo by implanting cells into which the antibody gene has been introduced into the abdominal cavity of an animal and the like.

As in vivo production systems, there can be mentioned those which employ animals and those which employ plants. When animals are used, there are the production systems which employ mammals and insects.

As mammals, goats, pigs, sheep, mice, and cattle can be used (Vicki Glaser, SPECTRUM Biotechnology Applications, 1993). Also as insects, silkworms can be used. When plants are used, tabacco, for example, can be used.

Antibody genes are introduced into these animals or plants, and the antibodies are produced in such animals or plants, and recovered. For example, an antibody gene is inserted into the middle of the gene encoding protein which is inherently produced in the milk such as goat β casein to prepare fusion genes. DNA fragments containing the fusion gene into which the antibody gene has been inserted are injected into a goat embryo, and the embryo is introduced into a female goat. The desired antibody is obtained from the milk produced by the transgenic goat borne to the goat who received the embryo or offspring thereof. In order to increase the amount of milk containing the desired antibody produced by the transgenic goat, hormones may be given to the transgenic goat as appropriate. (Ebert, K. M. et al., Bio/Technology (1994) 12, 699-702).

When silkworms are used, baculovirus into which the desired antibody gene has been inserted is infected to the silkworm, and the desired antibody can be obtained from the body fluid of the silkworm (Maeda, S. et al., Nature (1985) 315, 592-594). Moreover, when tabacco is used, the desired antibody gene is inserted into an expression vector for plants, for example pMON 530, and then the vector is introduced into a bacterium such as *Agrobacterium tumefaciens*. The bacterium is then infected to tabacco such as *Nicotiana tabacum* to obtain the desired antibody from the leaves of the tabacco (Julian, K.-C. Ma et al., Eur. J. Immunol. (1994) 24, 131-138).

When antibody is produced in in vitro or in vivo production systems, as described above, DNA encoding the heavy chain (H chain) or the light chain (L chain) of antibody may be separately integrated into an expression vector and the hosts are transformed simultaneously, or DNA encoding the H chain and the L chain may be integrated into a single expression vector and the host is transformed therewith (see International Patent Publication WO 94-11523).

Antibodies for use in the present invention may be antibody fragments or modified versions thereof as long as they are preferably used. For example, as fragments of antibody, there may be mentioned Fab, F(ab')$_2$, Fv or single-chain Fv (scFv) in which Fv's of H chain and L chain were ligated via a suitable linker.

Specifically, antibodies are treated with an enzyme, for example, papain or pepsin, to produce antibody fragments, or genes encoding these antibody fragments are constructed, and then introduced into an expression vector, which is expressed in a suitable host cell (see, for example, Co, M. S. et al., J. Immunol. (1994) 152, 2968-2976; Better, M. and Horwitz, A. H., Methods in Enzymology (1989) 178, 476-496; Plucktrun, A. and Skerra, A., Methods in Enzymology (1989) 178, 476-496; Lamoyi, E., Methods in Enzymology (1986) 121, 652-663; Rousseaux, J. et al., Methods in Enzymology (1986) 121, 663-669; Bird, R. E. et al., TIBTECH (1991) 9, 132-137).

scFv can be obtained by ligating the V region of H chain and the V region of L chain of antibody. In the scFv, the V region of H chain and the V region of L chain are preferably ligated via a linker, preferably a peptide linker (Huston, J. S. et al., Proc. Natl. Acad. Sci. USA (1988) 85, 5879-5883). The V region of H chain and the V region of L chain in the scFv may be derived from any of the above-mentioned antibodies. As the peptide linker for ligating the V regions, any single-chain peptide comprising, for example, 12-19 amino acid residues may be used.

DNA encoding scFv can be obtained using DNA encoding the H chain or the H chain V region of the above antibody and DNA encoding the L chain or the L chain V region of the above antibody as the template by amplifying the portion of the DNA encoding the desired amino acid sequence among the above sequences by the PCR technique with the primer pair specifying the both ends thereof, and by further amplifying the combination of DNA encoding the peptide linker portion and the primer pair which defines that both ends of said DNA are ligated to the H chain and the L chain, respectively.

Once DNAs encoding scFv are constructed, an expression vector containing them and a host transformed with said expression vector can be obtained by the conventional methods, and scFv can be obtained using the resultant host by the conventional methods.

These antibody fragments can be produced by obtaining the gene thereof in a similar manner to that mentioned above and by allowing it to be expressed in a host. "Antibody" as used in the claim of the present application encompasses these antibody fragments.

As modified antibodies, antibodies associated with various molecules such as polyethylene glycol (PEG) can be used. "Antibody" as used in the claim of the present application encompasses these modified antibodies. These modified antibodies can be obtained by chemically modifying the antibodies thus obtained. These methods have already been established in the art.

Antibodies produced and expressed as described above can be separated from the inside or outside of the host cell and then may be purified to homogeneity. Separation and purification of the antibody for use in the present invention may be accomplished by affinity chromatography. As the column used for such affinity chromatography, there can be mentioned Protein A column and Protein G column. Examples of the carriers used in the Protein A column are Hyper D, POROS, Sepharose F. F. and the like. Alternatively, methods for separation and purification conventionally used for proteins can be used without any limitation.

Separation and purification of the antibody for use in the present invention may be accomplished by combining, as appropriate, chromatography other than the above-mentioned affinity chromatography, filtration, ultrafiltration, salting-out, dialysis and the like. Chromatography includes, for example, ion exchange chromatography, hydrophobic chromatography, gel-filtration and the like. These chromatographies can be applied into high performance liquid chromatography (HPLC). Alternatively, reverse-phase HPLC can be used.

The concentration of antibody obtained in the above can be determined by the measurement of absorbance or by the enzyme-linked immunosorbent assay (ELISA) and the like. Thus, when absorbance measurement is employed, a sample is appropriately diluted with PBS(−) and then the absorbance is measured at 280 nm, followed by calculation using the absorption coefficient of 1.35 OD at 1 mg/ml. When the ELISA method is used, measurement is conducted as follows. Thus, 100 µl of goat anti-human IgG (manufactured by TAGO) diluted to 1 µg/ml in 0.1 M bicarbonate buffer, pH 9.6, is added to a 96-well plate (manufactured by Nunc), and is incubated overnight at 4° C. to immobilize the antibody. After blocking, 100 µl each of appropriately diluted antibody of the present invention or a sample containing the antibody, or 100 µl of human IgG (manufactured by CAPPEL) as the standard is added, and incubated at room temperature for 1 hour.

After washing, 100 µl of 5000-fold diluted alkaline phosphatase-labeled anti-human IgG antibody (manufactured by BIO SOURCE) is added, and incubated at room temperature for 1 hour. After washing, the substrate solution is added and incubated, followed by the measurement of absorbance at 405 nm using the MICROPLATE READER Model 3550 (manufactured by Bio-Rad) to calculate the concentration of the desired antibody.

The altered IL-6 for use in the present invention has an activity of binding to IL-6 receptor and does not transmit the biological activity of IL-6. Thus, the altered IL-6, though it competes with IL-6 receptor for binding to IL-6, does not transmit the biological activity of IL-6, and thereby it blocks signal transduction by IL-6.

Altered IL-6 may be constructed through the introduction of mutation by replacing amino acid residues of the amino acid sequence of IL-6. IL-6, the source of the altered IL-6, may be of any origin, but when the antigenicity is to be considered, it is preferably human IL-6.

Specifically, the secondary structure of IL-6 is predicted using a known molecular modeling program of the amino acid sequence, for example WHATIF (Vriend et al., J. Mol. Graphics (1990), 8, 52-56), and the overall effects on the amino acid residue to be replaced is evaluated. After an appropriate amino acid residue was determined, mutation is introduced by the commonly used polymerase chain reaction (PCR) method using a vector containing the base sequence encoding human IL-6 gene thereby to obtain a gene encoding altered IL-6. This is then integrated, as desired, into an appropriate expression vector, from which altered IL-6 can be obtained according to the expression, production and purification of said recombinant antibody.

Specific examples of the altered IL-6 are disclosed in Brakenhoff et al., J. Biol. Chem. (1994) 269, 86-93, and Savino et al., EMBO J. (1994) 13, 1357-1367, WO 96-18648, and WO 96-17869.

The IL-6 partial peptide or the IL-6 receptor partial peptide for use in the present invention has an activity of binding to IL-6 receptor or IL-6, respectively, and does not transmit the biological activity of IL-6. Thus, the IL-6 partial peptide or the IL-6 receptor partial peptide binds to IL-6 receptor or IL-6, respectively, and thereby capture it. As a result, they do not transmit the biological activity of IL-6, and block signal transduction of IL-6.

The IL-6 partial peptide or the IL-6 receptor partial peptide is a peptide comprising some or all of the amino acid sequence of the region involved in the binding to IL-6 and IL-6 receptor in the amino acid sequence of IL-6 or IL-6 receptor. Such a peptide generally comprises 10-80, preferably 20-50, and more preferably 20-40 amino acid residues.

The IL-6 partial peptide or the IL-6 receptor partial peptide can be constructed by specifying the region involved in the binding to IL-6 and IL-6 receptor in the amino acid sequence of IL-6 or IL-6 receptor, and by producing some or all of the amino acid sequence by a conventional method such as a genetic engineering technology or a peptide synthesis method.

In order to prepare the IL-6 partial peptide or the IL-6 receptor partial peptide by a genetic engineering technology, the DNA sequence encoding the desired peptide is integrated into an expression vector, from which the peptide can be obtained by the expression, production, and purification of said recombinant antibody.

Preparation of the IL-6 partial peptide or the IL-6 receptor partial peptide by the peptide synthesis method can be effected using a method commonly used in peptide synthesis such as the solid phase synthesis or the liquid phase synthesis.

Specifically the method described in Zoku-Iyakuhin no Kaihatsu (Sequel to Development of Pharmaceuticals), Vol. 14, Peputido Gousei (Peptide Synthesis), edited by Haruaki Yajima, Hirokawa Shoten, 1991, may be used. The solid phase synthesis method used includes, for example, a reaction in which an amino acid corresponding to the C-terminal of the peptide to be synthesized is coupled to a support which is insoluble in organic solvents, and then an amino acid in which an α-amino group or a side chain functional group has been protected with an appropriate protecting group is condensed one amino acid at a time from the C-terminal to the N-terminal direction, and a reaction in which said protecting group of the α-amino group of the amino acid or the peptide coupled to the resin is eliminated is alternately repeated to elongate the peptide chain. The solid phase peptide synthesis methods are divided into the Boc method and the Fmoc method depending on the type of protecting group to be used.

After the synthesis of the desired peptide is complete, a deprotection reaction and a reaction for cleaving the peptide chain from the support is carried out. For cleavage from the peptide chain, hydrogen fluoride or trifuluoromethanesulfonic acid in the Boc method and TFA in the Fmoc method are generally used. In the Boc method, for example, the above peptide resin is treated in hydrogen fluoride in the presence of anisole. Subsequently, the protecting group is eliminated and the peptide is recovered by cleaving from the support. By lyophilizing this, crude peptide can be obtained. On the other hand, in the Fmoc method, TFA, for example, is used in a manner similar to the above to effect the deprotection reaction and the cleavage reaction of the peptide from the support.

The crude peptide thus obtained can be applied to HPLC for its separation and purification. Its elution can be carried out in a water-acetonitrile solvent system that is commonly used for protein purification under an optimum condition. The fraction corresponding to the peak of the profile of the chromatography obtained is collected and lyophilized. The peptide fraction thus purified is identified by subjecting it to the analysis of molecular weight by mass spectroscopic analysis, the analysis of amino acid composition, or the analysis of amino acid sequence, and the like.

Specific examples of the IL-6 partial peptide or the IL-6 receptor partial peptide are disclosed in Japanese Unexamined Patent Publication (Kokai) 2 (1990)-188600, Japanese Unexamined Patent Publication (Kokai) 7 (1995)-324097, Japanese Unexamined Patent Publication (Kokai) 8 (1996)-311098, and United States Patent Publication U.S. Pat. No. 5,210,075.

The activity of the IL-6 antagonist for use in the present invention can be evaluated using a conventionally known method. Specifically, the IL-6-dependent cell MH60.BSF2 is cultured, to which IL-6 is added, and the activity can be evaluated using the incorporation of $^3$H-thymidine into the IL-6-dependent cell in the coexistence of the IL-6 antagonist. Alternatively, evaluation can be effected by culturing U266, an IL-6 receptor-expressing cell, adding thereto $^{125}$I-labeled IL-6 and an IL-6 antagonist at the same time, and then by determining the $^{125}$I-labeled IL-6 bound to the IL-6 receptor-expressing cell. In the above assay system, a negative control group containing no IL-6 antagonists, in addition to the group in which an IL-6 receptor antagonist is present, is set up, and the results obtained for them are compared to evaluate the IL-6-inhibiting activity of the IL-6 receptor antagonist.

In order to confirm the effects accomplished by the present invention, an IL-6 antagonist for use in the present invention is administered to animals that developed pancreatitis after an overdose of caerulein, and the effect of suppressing pancreatic edema and of improving the weight of the pancreas can be evaluated. As additional effects of the present invention, there are effects of preventing pancreatitis or the recurrence of pancreatitis.

The administration of caerulein to induce pancreatitis, for example, may be carried out according to the method described in the Example below. Animals in which pancreatitis is induced may be those commonly used in experiments such as mice and rats.

As described in the Example below, in the animals that developed pancreatitis, the administration of IL-6 receptor antibody resulted in suppression of the pancreas weight and improvement in the edema of the pancreas, and thus it was revealed that IL-6 antagonists such as anti-IL-6 receptor antibody exert a therapeutic effect on pancreatitis.

The subject to be treated in the present invention is mammals. The subject to be treated is preferably humans.

The preventive or therapeutic agents of the present invention may be administered, either orally or parenterally, systemically or locally. For example, intravenous injection such as drip infusion, intramuscular injection, intraperitoneal injection, subcutaneous injection, suppositories, intestinal lavage, oral enteric coated tablets, and the like can be selected, and the method of administration may be chosen, as appropriate, depending on the age and the conditions of the patient. The effective dosage is chosen from the range of 0.01 mg to 100 mg per kg of body weight per administration. Alternatively, the dosage in the range of 1 to 1000 mg, preferably 5 to 50 mg per patient may be chosen.

The preventive or therapeutic agents for pancreatitis of the present invention may contain pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but are not limited to, the above or combinations thereof depending on the dosage form.

EXAMPLES

The present invention will now be explained in more detail with reference to the examples, reference examples, and experiments. It should be noted, however, that the present invention is not limited to them in any way.

Example 1

To B6-hIL-6 transgenic mice or B6 mice (littermates of hIL-6 T transgenic mice) (Clinical Immunology and Immunopathology, 82: 117-124, 1997), caerulein (manufactured by Kyowa Hakko) dissolved in physiological saline at 50 µg/kg was intraperitoneally given every hour for 7 times. An anti-mouse IL-6 receptor monoclonal antibody M16-1 was administered to the mice at 1 mg/mouse via the tail vein immediately before caerulein administration.

Figure 1:
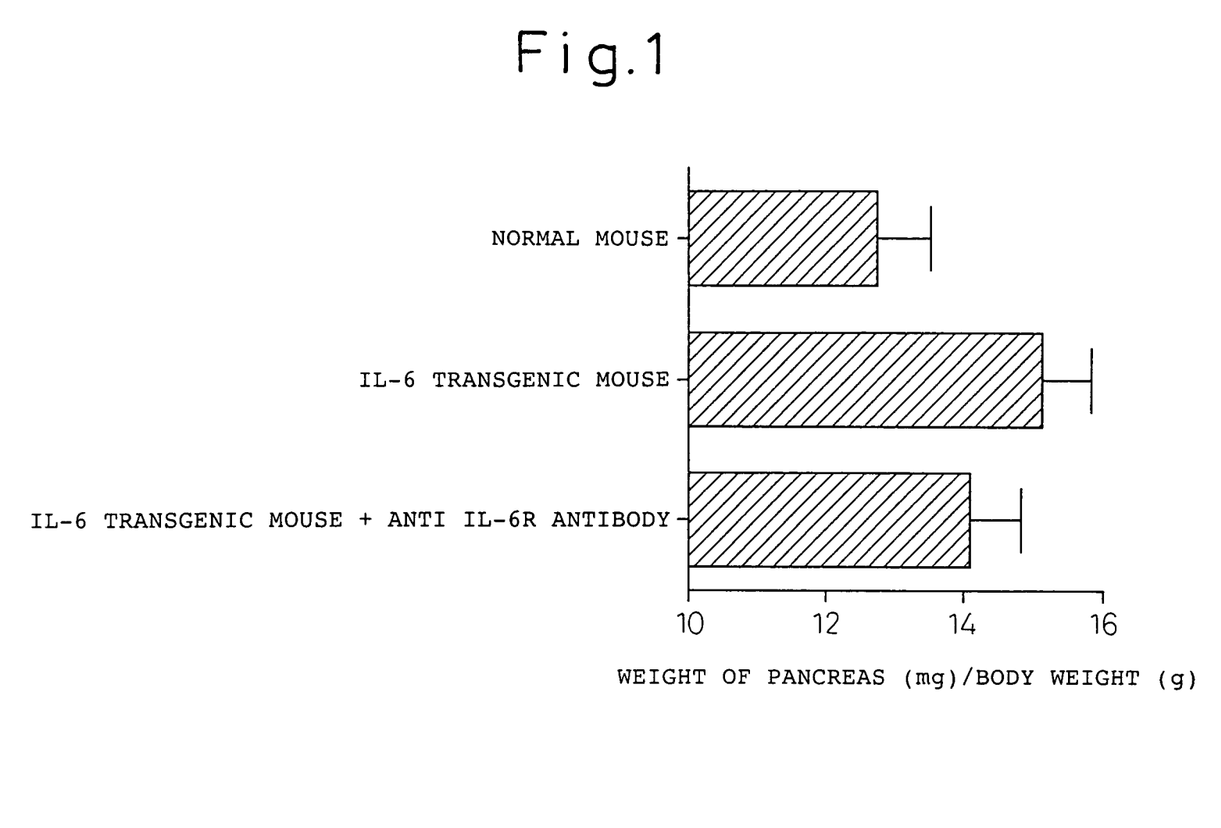
FIG. 1 shows that caerulein administration causes pancreatic edema resulting in the increased weight of the pancreas in IL-6 transgenic mice as compared to normal mice. It also shows that the above effect is suppressed by the administration of anti-IL-6 antibody.
Figure 2:
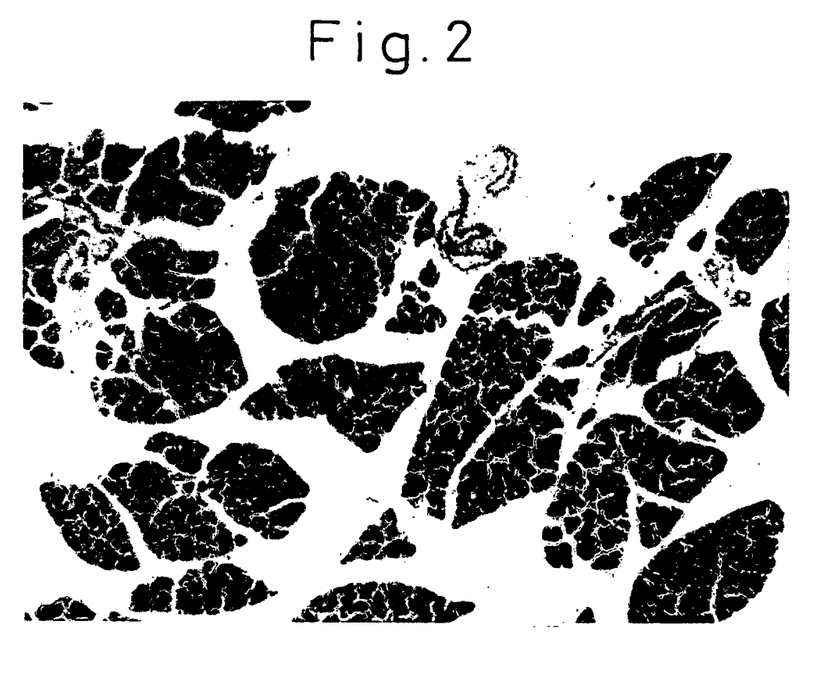
FIG. 2 is a micrograph of the pancreatic tissue of a normal mouse that developed acute pancreatitis by caerulein administration.
Figure 3:
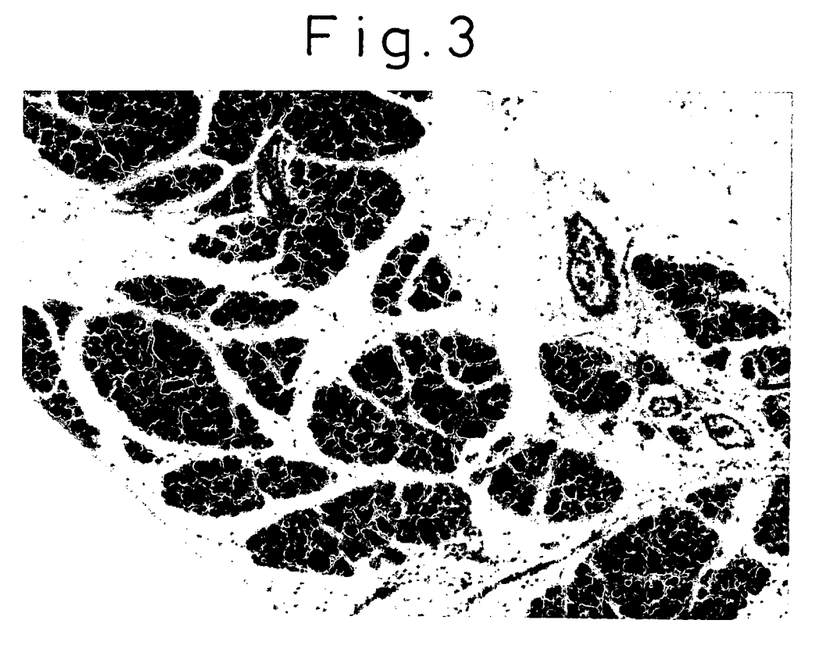
FIG. 3 is a micrograph of the pancreatic tissue of an IL-6 transgenic mouse that developed acute pancreatitis by caerulein administration.
Figure 4:
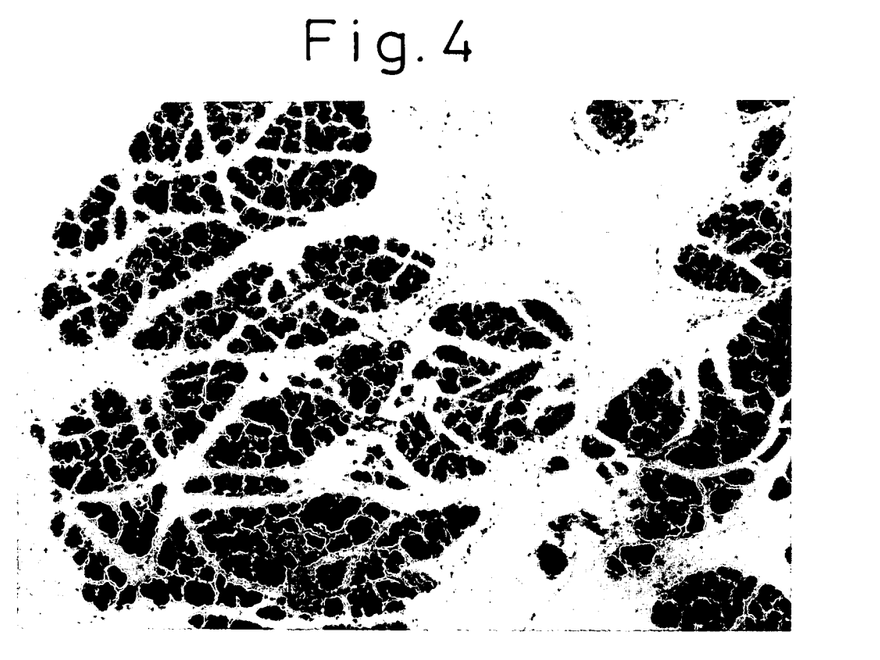
FIG. 4 is a micrograph of the pancreatic tissue of an IL-6 transgenic mouse that developed acute pancreatitis by caerulein administration and that received MR16-1 as well. As compared to the caerulein-induced pancreatitis in the normal mouse in FIG. 2, the caerulein-induced pancreatitis is aggravated (thus, enhanced edema in the interstitial tissue and enhanced infiltration in inflammatory cells) in the IL-6 transgenic mouse in FIG. 3.

As the control, the solvent (PBS) for the antibody was used. Eight hours later, the mice were euthanized to observe the weight of the pancreas, serum amylase, and the histology of the pancreas. The weight of the pancreas and body weight are shown in FIG. 1. The histology of the pancreas is shown in FIGS. 2-4. Serum amylase was measured using the iodostarch (blue starch) method. For the histology of the pancreas, a paraffin block of the pancreas was prepared and stained with hematoxylin eosin (HE) stain for microscopic observation.

In the IL-6 transgenic mice, the weight gain of the pancreas induced by caerulein administration was more pronounced as compared to the litter mate (normal mice).

Visual inspection also revealed that edema was more advanced as well as pancreatitis. By administering MR16-1 to the IL-6 transgenic mice, the weight gain of the pancreas induced by caerulein administration was suppressed. Histological comparison of the IL-6 transgenic mouse group (FIG. 3) and the normal mouse group (FIG. 2) has shown that areas of the edema etc. were smaller in the normal mice and the regions affected by neutrophil infiltration etc. were smaller. This indicates that the administration of MR16-1 resulted in improvement (FIG. 4). Thus, since the effect of anti-IL-6 receptor monoclonal antibody was observed in the mouse model of caerulein-induced acute pancreatitis, IL-6 antagonists such as anti-IL-6 receptor antibody are effective, by suppressing the effects of IL-6, in treatment, amelioration of severity, and prevention of onset of acute pancreatitis.

Example 2

Figure 5:
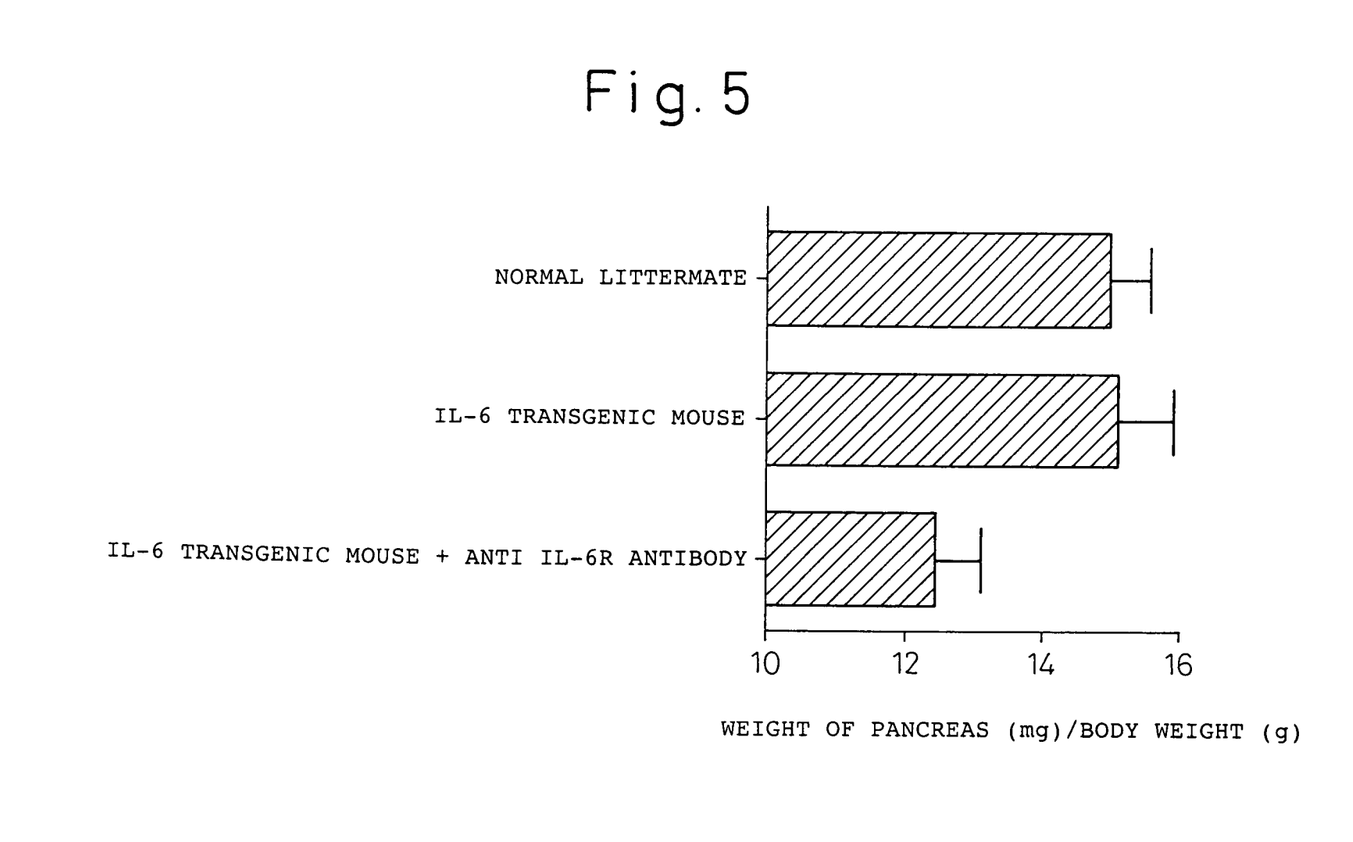
FIG. 5 shows that the increase in the weight of the pancreas in an IL-6 transgenic mouse induced by the administration of LPS and caerulein can be suppressed by the administration of an anti-IL-6 receptor antibody.

To B6-hIL-6 transgenic mice or B6 mice (littermates of hIL-6 T transgenic mice) (Clinical Immunology and Immunopathology, 82: 117-124, 1997), caerulein (manufactured by Kyowa Hakko) dissolved in physiological saline at 50 µg/kg was intraperitoneally given seven times at hourly intervals. In order to induce severe pancreatitis, LPS (lipopolysaccharide, manufactured by Sigma) was intraperitoneally given at 1 mg/ml concurrently with the initial caerulein administration. Anti-mouse IL-6 receptor monoclonal antibody M16-1 was administered to the mice at 1 mg/mouse via the tail vein 10 minutes before the initial caerulein administration. As the control, the solvent (PBS) for the antibody was used. Eight hours later, the mice were euthanized to measure the weight of the pancreas. The weight of the pancreas and body weight are shown in FIG. 5.

In severe pancreatitis induced in the IL-6 transgenic mice, MR16-1 administration caused a pronounced improvement effect. Thus, in the mouse model of severe acute pancreatitis induced by caerulein and LPS, IL-6 antagonists such as anti-IL-6 receptor antibody are effective, by suppressing the effects of IL-6, in treatment, amelioration of severity, and prevention of onset of severe acute pancreatitis.

Reference Example 1

Preparation of Human Soluble IL-6 Receptor

Soluble IL-6 receptor was prepared by the PCR method using a plasmid pBSF2R.236 containing cDNA that encodes IL-6 receptor obtained according to the method of Yamasaki et al., (Yamasaki, K. et al., Science (1988) 241, 825-828). Plasmid pBSF2R.236 was digested with a restriction enzyme Sph I to obtain the cDNA of IL-6 receptor, which was then inserted into mpl8 (manufactured by Amersham). Using a synthetic oligoprimer designed to introduce a stop codon into the cDNA of IL-6 receptor, a mutation was introduced into the cDNA of IL-6 receptor by the PCR method using the in vitro Mutagenesis System (manufactured by Amersham). The procedure resulted in the introduction of a stop codon to the amino acid at position 345, and gave cDNA encoding soluble IL-6 receptor.

In order to express the cDNA of soluble IL-6 receptor in CHO cells, it was ligated to plasmid pSV (manufactured by Pharmacia) to obtain plasmid pSVL344. The cDNA of soluble IL-6 receptor that was cleaved with Hind III-Sal I was inserted to plasmid pECEdhfr containing the cDNA of dhfr to obtain plasmid pECEdhfr344 that can be expressed in the CHO cells.

Ten µg of plasmid pECEdhfr344 was transfected to a dhfr-CHO cell line DXB-11 (Urlaub et al., Proc. Natl. Acad. Sci. USA (1980) 77, 4216-4220) by the calcium phosphate precipitation method (Chen C. et al., Mol. Cell. Biol. (1987) 7, 2745-2751). The transfected CHO cells were cultured for 3 weeks in a nucleoside-free α MEM selection medium containing 1 mM glutamine, 10% dialyzed FCS, 100 U/ml penicillin, and 100 µg/ml streptomycin.

The selected CHO cells were screened by the limiting dilution method to obtain a single CHO cell clone. The CHO cell clone was amplified in 20 nM-200 nM methotrexate (MTX) to obtain a CHO cell line 5E27 that produces human soluble IL-6 receptor. The CHO cell line 5E27 was cultured in an Iscov-modified Dulbecco's medium (IMDM, manufactured by Gibco) containing 5% FBS. The culture supernatant was collected and the concentration of soluble IL-6 receptor in the culture supernatant was determined by ELISA. The result confirmed that soluble IL-6 receptor is present in the culture supernatant.

Reference Example 2

Preparation of Human IL-6 Antibody

Ten µg of the recombinant IL-6 (Hirano et al., Immunol. Lett., 17:41, 1988) was immunized to BALB/c mice together with Freund's complete adjuvant, and this was repeated every week until anti-IL-6 antibody could be detected in the serum. Immune cells were extracted from local lymph node and were then fused with a myeloma cell line P3U1 using polyethylene glycol 1500. Hybridomas were selected according to the method of Oi et al. (Selective Methods in Cellular Immunology, W. H. Freeman and Co., San Francisco, 351, 1980) that employs the HAT medium, and the hybridoma that produces human IL-6 antibody was established.

The hybridoma that produces human IL-6 antibody was subjected to IL-6 binding assay as follows. Thus, a 96-well microtiter plate (manufactured by Dynatech Laboratories, Inc., Alexandria, Va.) made of flexible polyvinyl was coated with 100 µl of goat anti-mouse Ig (10 µl/ml, manufactured by Cooper Biomedical, Inc., Malvern, Pa.) overnight at 4° C. Subsequently, the plate was treated with 100 µl of PBS containing 1% bovine serum albumin (BSA) at room temperature for 2 hours.

After washing it in PBS, 100 µl of the hybridoma culture supernatant was added to each well, and then was incubated overnight at 4° C. The plate was washed, $^{125}$I-labeled recombinant IL-6 was added to each well to a concentration of 2000 cpm/0.5 ng/well, and then radioactivity of each well after washing was determined by a gamma counter (Beckman Gamma 9000, Beckman Instruments, Fullerton, Calif.). Of 216 hybridoma clones, 32 were positive in the IL-6 binding assay. From these clones, stable MH166.BSF2 was finally obtained. Anti-IL-6 antibody MH166 produced by said hybridoma has a subtype of IgG1 κ.

Then, the IL-6-dependent mouse hybridoma clone MH60.BSF2 was used to examine a neutralizing activity with respect to the growth of the hybridoma by MH166 antibody. MH60.BSF2 cells were dispensed to $1 \times 10^4/200$ µl/well, and samples containing MH166 antibody were added thereto, cultured for 48 hours, 0.5 µCi/well of $^3$H-thymidine (New England Nuclear, Boston, Mass.) was added, and the culturing was continued for further 6 hours. The cells were placed on a glass filter paper and were treated by the automatic harvester (Labo Mash Science Co., Tokyo, Japan). As the control, rabbit anti-IL-6 antibody was used.

As a result, MH166 antibody inhibited, in a dose dependent manner, the incorporation of $^3$H-thymidine of MH60.BSF2 cells induced by IL-6. This revealed that MH166 antibody neutralizes the activity of IL-6.

Reference Example 3

Preparation of Human Anti-IL-6 Receptor Antibody

Anti-IL-6 receptor antibody MT18 prepared by the method of Hirata et al. (Hirata, Y. et al. J. Immunol., 143, 2900-2906, 1989) was bound to CNBr-activated Sepharose 4B (manufactured by Pharmacia Fine Chemicals, Piscataway, N.J.) according to the attached regimen, and IL-6 receptor (Yamasaki, K. et al., Science (1988) 241, 825-828) was purified. A human myeloma cell line U266 was solubilized with 1 mM p-para-aminophenyl methane sulfonyl fluoride hydrochloride (manufactured by Wako Chemicals) containing 1% digitonin (manufactured by Wako Chemicals), 10 mM triethanolamine (pH 7.8) and 0.15 M NaCl (digitonin buffer), and mixed with MT18 antibody bound to Sepharose 4B beads. Then, the beads were washed six times with the digitonin buffer to prepare the partially purified IL-6 receptor for use in immunization.

BALB/c mice were immunized four times, at ten-day intervals, with the above partially purified IL-6 receptor obtained from $3 \times 10^9$ U266 cells, and then a hybridoma was prepared using a standard method. The hybridoma culture supernatant from the growth-positive well was tested for its activity of binding to IL-6 receptor according to the method described below. $5 \times 10^7$ U266 cells were labeled with $^{35}$S-methionine (2.5 mCi) and were solubilized with the above digitonin buffer. The solubilized U266 cells were mixed with a 0.04 ml volume of MT18 antibody bound to Sepharose 4B beads, and then were washed six times with the digitonin buffer. $^{35}$S-methionine-labeled IL-6 receptor was eluted with 0.25 ml of the digitonin buffer (pH 3.4) and was neutralized in 0.025 ml of 1M Tris (pH 7.4).

0.05 ml of the hybridoma culture supernatant was mixed with 0.1 ml of Protein G Sepharose (manufactured by Pharmacia). After washing, Sepharose was incubated with 0.005 ml of $^{35}$S-labeled IL-6 receptor solution prepared as described above. The immunoprecipitate was analyzed by SDS-PAGE to determine the hybridoma culture supernatant that reacts with IL-6 receptor. As a result, the reaction-positive hybridoma clone PM-1 was established. The antibody produced from the hybridoma PM-1 has a subtype of IgG1κ.

The inhibitory activity of IL-6 binding of the antibody produced by the hybridoma PM-1 to human IL-6 receptor was studied using the human myeloma cell line U266. A human recombinant IL-6 was prepared from *E. coli* (Hirano et al., Immunol. Lett., 17:41-45, 1988), and was labeled with $^{125}$I using the Bolton-Hunter reagent (New England Nuclear, Boston, Mass.) (Taga, T. et al., J. Exp. Med. (1987) 166, 967-981). $4 \times 10^5$ U266 cells were cultured with the culture supernatant of 70% (v/v) hybridoma PM-1 together with 14,000 cpm of $^{128}$I-labeled IL-6 for one hour. Seventy µl of the sample was layered on 300 µl FCS in a 400 µl microfuge polyethylene tube. After centrifugation, the radioactivity of the cell was determined.

The result revealed that the antibody produced by the hybridoma PM-1 inhibits the binding of IL-6 to IL-6 receptor.

Reference Example 4

Preparation of Mouse Anti-IL-6 Receptor Antibody

A monoclonal antibody directed against mouse IL-6 receptor was prepared according to the method described in Saito, et al., J. Immunol. (1993) 147, 168-173.

The CHO cells that produce mouse soluble IL-6 receptor were cultured in the IMDM culture liquid containing 10% FCS. From the culture supernatant, mouse soluble IL-6 receptor was purified using mouse soluble IL-6 receptor antibody RS12 (see Saito, et al., supra) and an affinity column fixed to Affigel 10 gel (manufactured by Biorad).

The mouse soluble IL-6 receptor (50 µg) thus obtained was mixed with Freund's complete adjuvant, which was then injected to the abdomen of Wistar rats. From 2 weeks after the administration, the animals were boosted with Freund's incomplete adjuvant. On day 45, the rat spleen cells were collected, and the cells at about $2 \times 10^8$ were fused with $1 \times 10^7$ mouse myeloma cells P3U1 using a 50% PEG1500 (manufactured by Boehringer Mannheim) according to the conventional method, and then were screened by the HAT culture medium.

After the culture supernatant was added to the plate coated with rabbit anti-rat IgG antibody (manufactured by Cappel), mouse soluble IL-6 receptor was reacted. Subsequently, using rabbit anti-mouse IL-6 receptor antibody and alkaline phosphatase-labeled sheep anti-rabbit IgG, hybridomas producing antibody directed against mouse soluble IL-6 receptor were screened by ELISA. After antibody production was confirmed, the hybridoma clones were subscreened twice to obtain a single hybridoma clone. The clone was designated as MR16-1.

The neutralizing activity of the antibody produced by the hybridoma on signal transduction of mouse IL-6 was examined by $^3$H-thymidine incorporation using MH60.BSF2 cells (Matsuda, T. et al., J. Immunol. (1988) 18, 951-956). To a 96-well plate, MH60.BSF2 cells were prepared at $1\times10^4$ cells/200 μl/well. To the plate were added 10 pg/ml mouse IL-6 and MR16-1 antibody or RS12 antibody at 12.3-1000 ng/ml, and then were cultured at 37° C. and 5% $CO_2$ for 44 hours and then 1 μCi/well of $^3$H-thymidine was added. After 4 hours, the incorporation of $^3$H-thymidine was measured. As a result, MR16-1 antibody suppressed the incorporation of $^3$H-thymidine of the MH60.BSF2 cells.

Thus, it was demonstrated that the antibody produced by the hybridoma MR16-1 inhibits the binding of IL-6 to IL-6 receptor.

INDUSTRIAL APPLICABILITY

In accordance with the present invention, it was shown that IL-6 antagonists such as anti-IL-6 receptor antibody have a therapeutic effect on pancreatitis. Thus, it was demonstrated that IL-6 antagonists are useful as a therapeutic agent for acute pancreatitis and the like.

The invention claimed is:

1. A method of treating acute pancreatitis which method comprises administering an interleukin-6 (IL-6) antagonist at an amount effective to treat acute pancreatitis to a subject in need of such treatment, wherein said IL-6 antagonist is an antibody directed against IL-6 receptor which blocks signal transduction of IL-6.

2. The method according to claim 1 in which the antibody directed against IL-6 receptor is a monoclonal antibody directed against IL-6 receptor.

3. The method according to claim 2 in which the antibody directed against IL-6 receptor is a monoclonal antibody directed against human IL-6 receptor.

4. The method according to claim 2 in which the antibody directed against IL-6 receptor is a monoclonal antibody directed against mouse IL-6 receptor.

5. The method according to claim 1 in which the antibody directed against IL-6 receptor is a recombinant antibody.

6. The method according to claim 3 in which the monoclonal antibody directed against human IL-6 receptor is PM-1 antibody.

7. The method according to claim 4 in which the monoclonal antibody directed against mouse IL-6 receptor is MR16-1 antibody.

8. The method according to claim 1 in which the antibody directed against IL-6 receptor is a chimeric antibody or a humanized antibody directed against IL-6 receptor.

9. The method according to claim 8 in which the humanized antibody directed against IL-6 receptor is a humanized PM-1 antibody.

10. A method of reducing pancreatic edema in pancreatitis which method comprises administering an effective amount of an IL-6 antagonist to a subject in need of such treatment, wherein said IL-6 antagonist binds to IL-6 receptor and inhibits the binding of IL-6 or gp 130 to the IL-6 receptor and which blocks signal transduction of IL-6.

11. A method of reducing pancreatic edema which method comprises administering an antibody directed against IL-6 receptor at an amount effective to reduce pancreatic edema to a subject in need of suppressing pancreatic edema, wherein said antibody blocks signal transduction of IL-6.

12. A method of ameliorating the severity of acute pancreatitis which method comprises administering to a subject in need of such treatment an interleukin-6 (IL-6) antagonist at an amount effective to ameliorate the severity of acute pancreatitis, wherein said IL-6 antagonist is an antibody directed against IL-6 receptor and which blocks signal transduction of IL-6.

* * * * *